US012806321B2

(12) United States Patent
Zaniboni

(10) Patent No.: US 12,806,321 B2
(45) Date of Patent: Nov. 24, 2026

(54) OXYGENATOR WITH GAS COMPARTMENT HEATER

(71) Applicant: Lifemotion S.r.l., Milan (IT)

(72) Inventor: Andrea Zaniboni, Mirandola (IT)

(73) Assignee: Lifemotion S.r.l., Milan (IT)

( * ) Notice: Subject to any disclaimer, the term of this patent is extended or adjusted under 35 U.S.C. 154(b) by 355 days.

(21) Appl. No.: 18/674,465

(22) Filed: May 24, 2024

(65) Prior Publication Data

US 2025/0360253 A1 Nov. 27, 2025

(51) Int. Cl.
*A61M 1/16* (2006.01)

(52) U.S. Cl.
CPC ........ *A61M 1/1698* (2013.01); *A61M 1/1625* (2014.02); *A61M 1/1629* (2014.02); *A61M 2202/0007* (2013.01); *A61M 2202/0014* (2013.01); *A61M 2202/0021* (2013.01); *A61M 2202/0208* (2013.01); *A61M 2202/0225* (2013.01); *A61M 2202/0413* (2013.01); *A61M 2205/10* (2013.01); *A61M 2205/127* (2013.01); *A61M 2205/3327* (2013.01); *A61M 2205/3368* (2013.01); *A61M 2205/3653* (2013.01); *A61M 2205/502* (2013.01)

(58) Field of Classification Search
CPC .............. A61M 1/1625; A61M 1/3666; A61M 1/1698; A61M 1/3623; A61M 1/1629; A61M 2202/0208; Y10S 128/03; Y10S 261/28
See application file for complete search history.

(56) References Cited

U.S. PATENT DOCUMENTS 4,948,560 A * 8/1990 Deguchi ............. A61M 1/1698 210/321.89
2019/0160217 A1* 5/2019 Marseille ............ A61M 1/1698
2019/0167882 A1* 6/2019 Matheis .............. A61M 1/1664

FOREIGN PATENT DOCUMENTS

EP 0183250 A2 6/1986
JP 3601861 B2 6/1996
JP 5674456 B2 7/2012

* cited by examiner

*Primary Examiner* — Ariana Zimbouski
(74) *Attorney, Agent, or Firm* — Nelson Mullins Riley & Scarborough LLP

(57) ABSTRACT

An oxygenation device for use with extracorporeal blood circulation is disclosed. The device includes an oxygenator housing having a blood inlet end cap having a blood inlet opening, a blood outlet end cap having a blood outlet opening, and a gas collector housing between the blood inlet opening and the blood outlet opening. The gas collector housing defines a gas compartment having a gas inlet chamber with a gas inlet port and a gas outlet chamber with a gas outlet port. Heating devices are disposed against the gas collector housing and include a first heating device in the gas inlet chamber and a second heating device in the gas outlet chamber. During operation of the oxygenation device, the heating devices heat the gas compartment.

20 Claims, 11 Drawing Sheets

OXYGENATOR WITH GAS COMPARTMENT HEATER

TECHNICAL FIELD

This disclosure relates to the field of devices for extracorporeal circulation of blood. More specifically, the disclosure relates to extracorporeal blood oxygenators and component of the blood oxygenators, such as features of a gas collector.

BACKGROUND

Blood extracorporeal circuits may include dual portions of an oxygenator and heat exchanger to exchange oxygen and carbon dioxide between blood and a gas mixture and exchange heat between blood and a heating or cooling fluid through the walls of semipermeable hollow fiber membranes. Blood contacts the outside surfaces of the hollow fibers, while the gas mixture and the heating/cooling fluid (e.g., a water solution) are circulated inside the hollow fiber lumens. In the devices using this technology, the hollow fibers may be organized in different ways. They may be in a single or multifilament form which is woven around a core to form a wound or bundled oxygenator, or they may be structured in mats wound around a core or stacked in parallel mat layers on top of one another without a core to form a stacked oxygenator. Various examples of this technology are well known in the technical field.

SUMMARY

In hollow fiber oxygenators, blood is circulated outside the fibers, while gas flows inside the fibers through lumens at a temperature generally lower than a temperature of the blood. The temperature of the gas within the fiber lumens varies along the length of the hollow fiber. For example, temperature of the gas increases in the first part of the fiber course close to gas inlet, reaches a temperature equal or close to blood temperature in the intermediate portion of the fibers. The gas is subjected to an abrupt decrease in temperature towards the gas outlet, where gas comes into contact with the oxygenator parts exposed to external ambient temperatures usually much colder than blood temperature. As a consequence, vapor contained in the gas and extracted with carbon dioxide from blood through the fiber microporosity may condensate and accumulate onto the inner surfaces of the fiber lumens and on the housing parts close to the surface of the oxygenator. This phenomenon is referred to as "wet lung" and can lead to reduced gas transfer capacity in the oxygenator, pressure conditions that lead to patient embolism, and inaccurate meter readings of key parameters.

Embodiments of the present invention include oxygenator having a heating device coupled to an oxygenator housing for a gas compartment to provide for a temperature conditioning of the gas compartment that is close to a temperature of the blood to avoid the potential issues presented with wet lung. In some embodiments, gas compartment is heated as gas enters the hollow fibers and as gas exits the hollow fibers to provide for a more efficient reduction of the wet lung phenomenon over heating just the gas compartment where gas exits the hollow fibers or gas entering the hollow fibers. In embodiments, the gas compartment is heated with low-profile, flexible thermofoil heating devices attached to the oxygenator housing within the gas compartment. This provides effective temperature conditioning without noticeably affecting gas pressure within the gas compartment.

Example 1 is an oxygenation device for use in connection with extracorporeal blood circulation, the device comprising: an oxygenator housing including a blood inlet end cap defining a blood inlet opening, a blood outlet end cap defining a blood outlet opening and a blood flow path between the blood inlet opening and the blood outlet opening, and a gas collector housing disposed between the blood inlet opening and the blood outlet opening, the gas collector housing defining a gas inlet port, a gas outlet port and a gas compartment having a gas inlet chamber in fluid communication with the gas inlet port and a gas outlet chamber in fluid communication with the gas outlet port; a plurality of hollow fibers disposed inside the oxygenator housing and along the blood flow path, the hollow fibers fluidly coupled to the gas compartment; and a plurality of heating devices disposed against the gas collector housing, the plurality of heating devices including a first heating device disposed in the gas inlet chamber and a second heating device disposed in the gas outlet chamber, wherein during operation of the oxygenation device, the plurality of heating devices are configured to heat the gas compartment.

Example 2 is the device of Example 1, wherein the plurality of hollow fibers disposed inside the housing include a plurality of stacked, mat layers of the hollow fibers.

Example 3 is the device of Example 1, wherein the oxygenator housing further comprises a heat exchanger housing for a heat exchanger module adjacent to the oxygenator housing.

Example 4 is the device of Example 3, wherein the heat exchanger housing defines a fluid inlet port and a fluid outlet port and is configured such that a H/C fluid may pass through the plurality of hollow fibers.

Example 5 is the device of Example 1, wherein the oxygenator housing is configured such that a gas mixture may enter through the gas inlet port, pass through the plurality of hollow fibers and exit through the gas outlet port.

Example 6 is the device of Example 1, and further comprising a temperature sensor disposed in the gas collector housing.

Example 7 is the device of Example 6, wherein the temperature sensor includes a first temperature sensor disposed in the gas inlet chamber and a second temperature sensor disposed in the gas outlet chamber.

Example 8 is the device of Example 7, and further comprising a remote monitoring unit communicatively coupled to each of the first and second temperature sensors.

Example 9 is the device of Example 8, wherein the remote monitoring unit is configured to operate the heating devices to heat the gas in the gas compartment to the temperature of blood in the device.

Example 10 is the device of Example 6, and further comprising a manifold coupled to the oxygenator housing to receive electrical leads from the heating device and the temperature sensor.

Example 11 is the device of Example 10, wherein the manifold includes an electrical connection.

Example 12 is the device of Example 1, wherein each of the plurality of heating device includes a flexible heating device having an electrical element disposed on a flexible electrically-insulative substrate.

Example 13 is the device of Example 12, wherein the gas compartment includes a generally cylindrical major inner surface defined in the gas inlet chamber and the gas outlet chamber, and the plurality of flexible heating devices are adhered to the major inner surface.

Example 14 is the device of Example 13, wherein the plurality of flexible heating devices are spaced-apart from the plurality of hollow fibers.

Example 15 is an oxygenation system for use in connection with extracorporeal blood circulation, the system comprising: an oxygenator housing including a blood inlet end cap defining a blood inlet opening, a blood outlet end cap defining a blood outlet opening and a blood flow path between the blood inlet opening and the blood outlet opening, and a gas collector housing disposed between the blood inlet opening and the blood outlet opening, the gas collector housing defining a gas inlet port, a gas outlet port and a gas compartment having a gas inlet chamber in fluid communication with the gas inlet port and a gas outlet chamber in fluid communication with the gas outlet port; a plurality of hollow fibers disposed inside the oxygenator housing and along the blood flow path, the hollow fibers fluidly coupled to the gas compartment; a plurality of heating devices disposed against the gas collector housing, the plurality of flexible heating elements including a first heating device disposed in the gas inlet chamber and a second heating device disposed in the gas outlet chamber; and a remote monitoring unit communicatively coupled to the plurality of heating devices, wherein during operation of the system the remote monitoring unit is configured to provide a heating signal to the plurality of heating devices to heat gas in the gas compartment.

Example 16 is the system of Example 15, and further comprising a temperature sensor disposed on the gas collector housing and communicatively coupled to the remote monitoring unit, wherein during operation of the system the remote monitoring is configured to receive a temperature signal from the temperature sensor on which to base the heating signal.

Example 17 is the system of Example 16, wherein the temperature sensor includes a first temperature sensor disposed in the gas inlet chamber and a second temperature sensor disposed in the gas outlet chamber, the first temperature sensor configured to provide a first temperature signal to the remote monitoring unit, and the second temperature sensor configured to provide a second temperature signal to the remote monitoring unit.

Example 18 is the system of Example 17, wherein the heating signal includes a first heating signal provided to the first heating device and a second heating signal provided to the second heating device.

Example 19 is the system of Example 18, wherein the remote monitoring unit provides the first heating signal is based on the first temperature signal and the second heating signal based on the second temperature signal.

Example 20 is the system of Example 15, wherein the plurality of hollow fibers disposed inside the housing include a plurality of stacked, mat layers of the hollow fibers.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
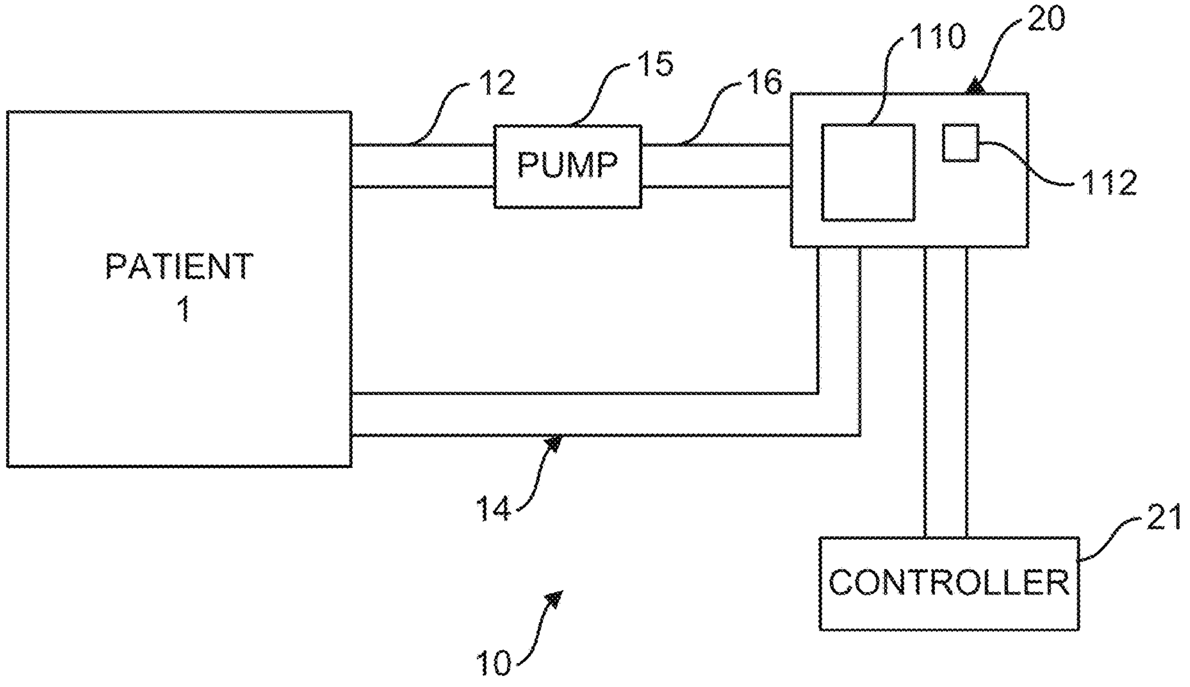
FIG. 1 is a schematic view of a patient undergoing extracorporeal blood circulation.

While the invention is amenable to various modifications and alternative forms, specific embodiments have been shown by way of example in the drawings and are described in detail below. The intention, however, is not to limit the invention to the embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), “about” and “approximately” may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or specific order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

FIG. 1 is a schematic view of an extracorporeal blood circulation system 10 (also referred to herein as an extracorporeal circuit 10) for supporting a patient 1 requiring extracorporeal blood circulation. In various embodiments, the patient 1 is connected through a first tubing 12 (also called a venous line) to the extracorporeal blood circuit 10 including a pump 15 to cause blood to be transferred from the patient 1, through the first tubing 12 and 16, to a mass transfer device 20, commonly referred to as an oxygenator device 20 (or oxygenator 20). Note that the oxygenator 20 may include one or both of an oxygenator module and a heat exchanger module.

The system 10 further includes a second tubing 14 (also called an arterial line) that extends from the oxygenator 20 to the patient 1 for transferring blood that has been circulated within the pump 15 and oxygenator 20 back to the patient 1. The extracorporeal circuit 10 includes a plurality of sensors which measure parameters like blood pressures, flow rate, temperatures, hematocrit, oxygen saturation and oxygen and carbon dioxide partial pressures of blood, that must be kept under control during the perfusion process. In general, and not exclusively, such sensors may be located pre- and/or post-oxygenator, depending on whether the quantities must be measured on the venous or the arterial side. They may be in direct contact with blood or may measure the quantities from the tubing outside and are electrically connected to a separate and remote control and monitoring unit 21 under operator (e.g., a perfusionist or other dedicated health personnel) control by means of an appropriate control system. The controller 21 can include a display and controls, such as buttons, knobs, and touch screen, to allow the operator to select various parameters or settings for the controller 21. In some embodiments, the controller 21 is electrically and mechanically coupled to the oxygenator device 20, and in other embodiments, the controller 21 is wirelessly coupled to the oxygenator device via communication circuitry in the controller 21 and mechanically coupled to the oxygenator device 20 to communicate via wireless telemetry.

In various embodiments, oxygen ($O_2$) and carbon dioxide ($CO_2$) are exchanged between blood and a gas mixture within the oxygenator device 20, such as via hollow fibers in fluid communication with a gas compartment as will be described further herein. The oxygenator device 20 includes a heating element coupled to the gas compartment to provide for temperature conditioning that is close to a temperature of the blood to avoid potential issues presented with wet lung. In some embodiments, the entire gas compartment is heated such that gas is warmed as it enters the hollow fibers and as it exits the hollow fibers to provide for a more efficient reduction of the wet lung phenomenon versus heating just one of the sides of the gas compartment (the side proximate gas entrance to the hollow fibers or the side proximate gas exit from the hollow fibers). In embodiments, the oxygenator device 20 includes a temperature sensor within the gas compartment operably coupled to the remote control and monitoring unit 21, and energy provided to operate the heating device is controlled by the remote control and monitoring unit in response to the temperature sensor. The oxygenator device 20, in certain embodiments, is also configured for exchanging temperature (hot or cool temperatures) between the blood and heating/cooling (H/C) fluid into a heat exchanger module included in the oxygenator device 20. In some embodiments, the H/C is water or a water solution.

Figure 2:
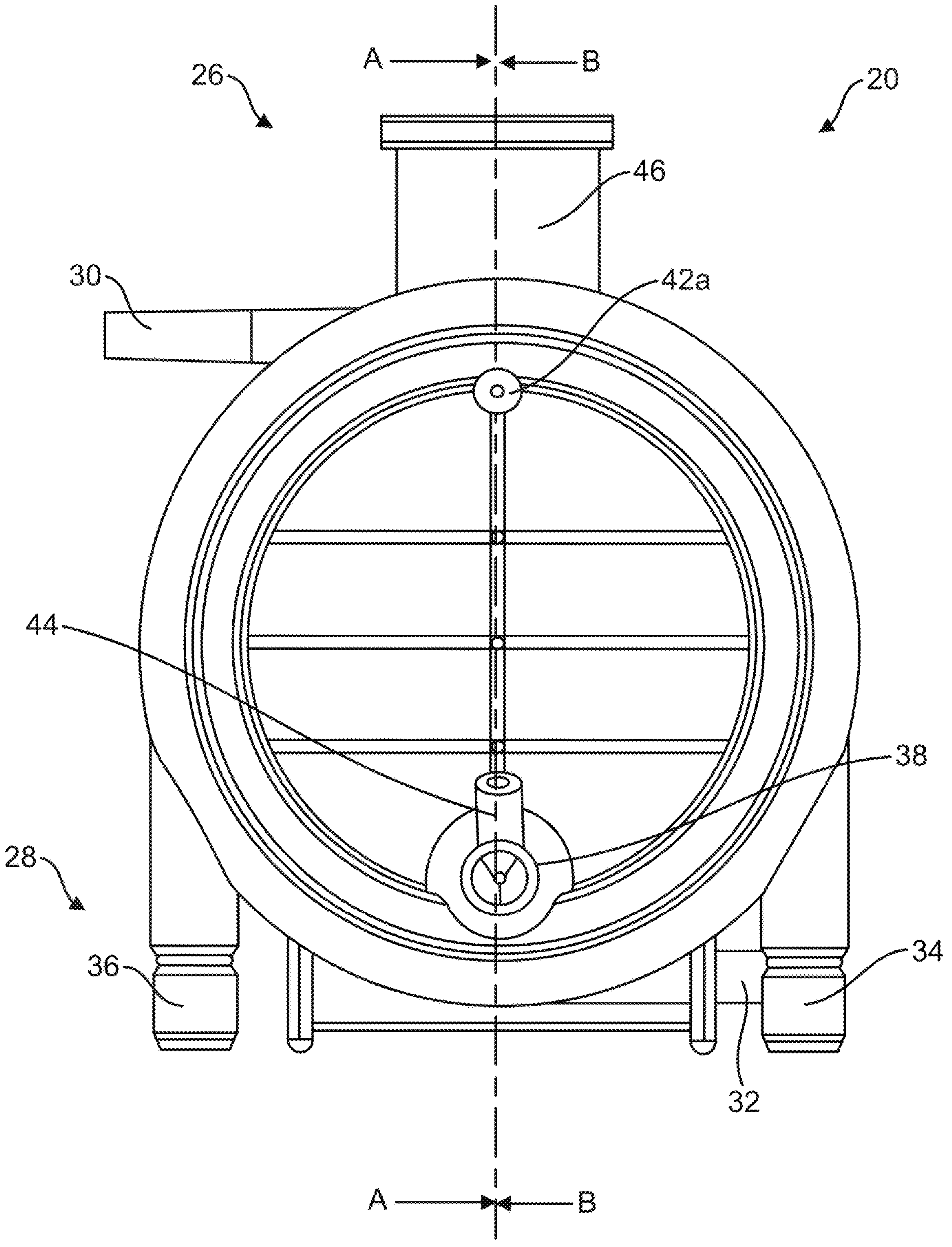
FIG. 2 is a schematic front view of an exemplary stacked oxygenator device.

FIG. 2 is a front view of an exemplary stacked oxygenator device 20 having an oxygenator module (not shown) and a heat exchanger module (not shown). The stacked oxygenator device 20 is provided for illustration, and the features of the present disclosure can be applied to other types of oxygenators such as bundled oxygenators. The oxygenator device 20 has an upper portion 26 and a lower portion 28. In various embodiments, the oxygenator 20 includes a gas inlet port 30 configured for receiving a gas mixture, a gas outlet port 32 configured for exporting a gas mixture, a H/C fluid inlet port 34 for receiving H/C fluid, an H/C fluid outlet port 36 for exporting H/C fluid, a blood inlet port 38 for receiving blood from the patient 1 through the tubing 16, and a blood outlet port (not shown) for exporting blood from the oxygenator device 20 back to the patient 1 through the tubing 14. The oxygenator device 20 further includes a venous sampling port 44 and a first purging port 42*a*, as will be described further with reference to FIG. 3. In some embodiments, the oxygenator device 20 additionally includes a bracket attachment 46 to allow for attachment and rotation of the oxygenator device 20 from the top. Alternatively, the bracket attachment 46 may also be coupled to the bottom so as to allow attachment and rotation of the oxygenator from the bottom.

Figure 3:
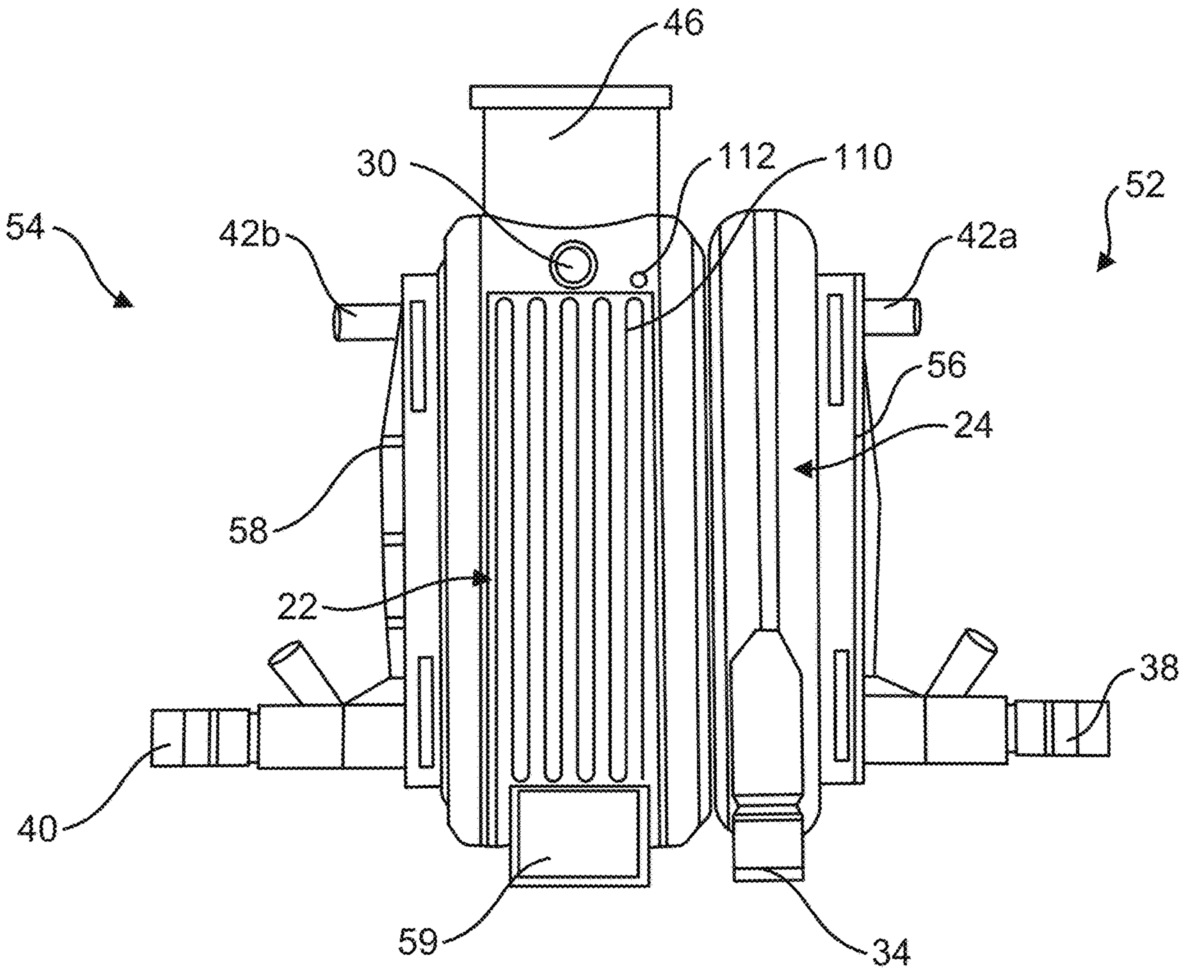
FIG. 3 is a lateral isometric view from the left of the oxygenator device of FIG. 2.

FIG. 3 is a side view, from the left of FIG. 2, of the oxygenator device 20. As illustrated, the oxygenator device 20 includes a front portion 52 and a rear portion 54. The front portion 52 includes a blood inlet end cap 56 coupled to a blood inlet port 38 configured for receiving blood from tubing 16 and the rear portion 54 includes a blood outlet end cap 58 coupled to a blood outlet port 40 for providing an exit for the blood to return to the patient 1 through the tubing 14. Additionally, as illustrated in FIG. 3, the oxygenator device 20 includes the gas inlet port 30 on the side surface of the oxygenator device 20. The oxygenator device 20 additionally includes a plurality of purging ports 42 including at least the first purging port 42*a* and a second purging port 42*b*. Purging ports 42*a*, 42*b* may allow for removal of air during an initial priming phase of the oxygenator device 20 prior to use with the patient. During operation, i.e., when blood and gas flow through the device 20, the purging ports 42*a*, 42*b* may be reopened for removing entrapped air from blood. Additionally, the purging ports 42*a*, 42*b* may be opening after operation of the device 20, i.e., when blood is no longer flowing through the device 20, to ensure proper emptying of any blood from the device 20 and returning it to the patient. The oxygenator device 20 may also include a pedestal 59 positioned on a bottom surface of the device 20 for supporting and stabilizing the device 20, if the bracket attachment 46, as shown in FIG. 2, is located at the top of the oxygenator.

As previously described with reference to FIG. 2, the oxygenator device 20 includes a front portion 52 and a rear portion 54. In these embodiments and as illustrated in FIG. 3, the front portion 52 encompasses at least a portion of the heat exchanger module 24 and the rear portion 54 encompasses at least a portion of the oxygenator module 22.

Figure 4:
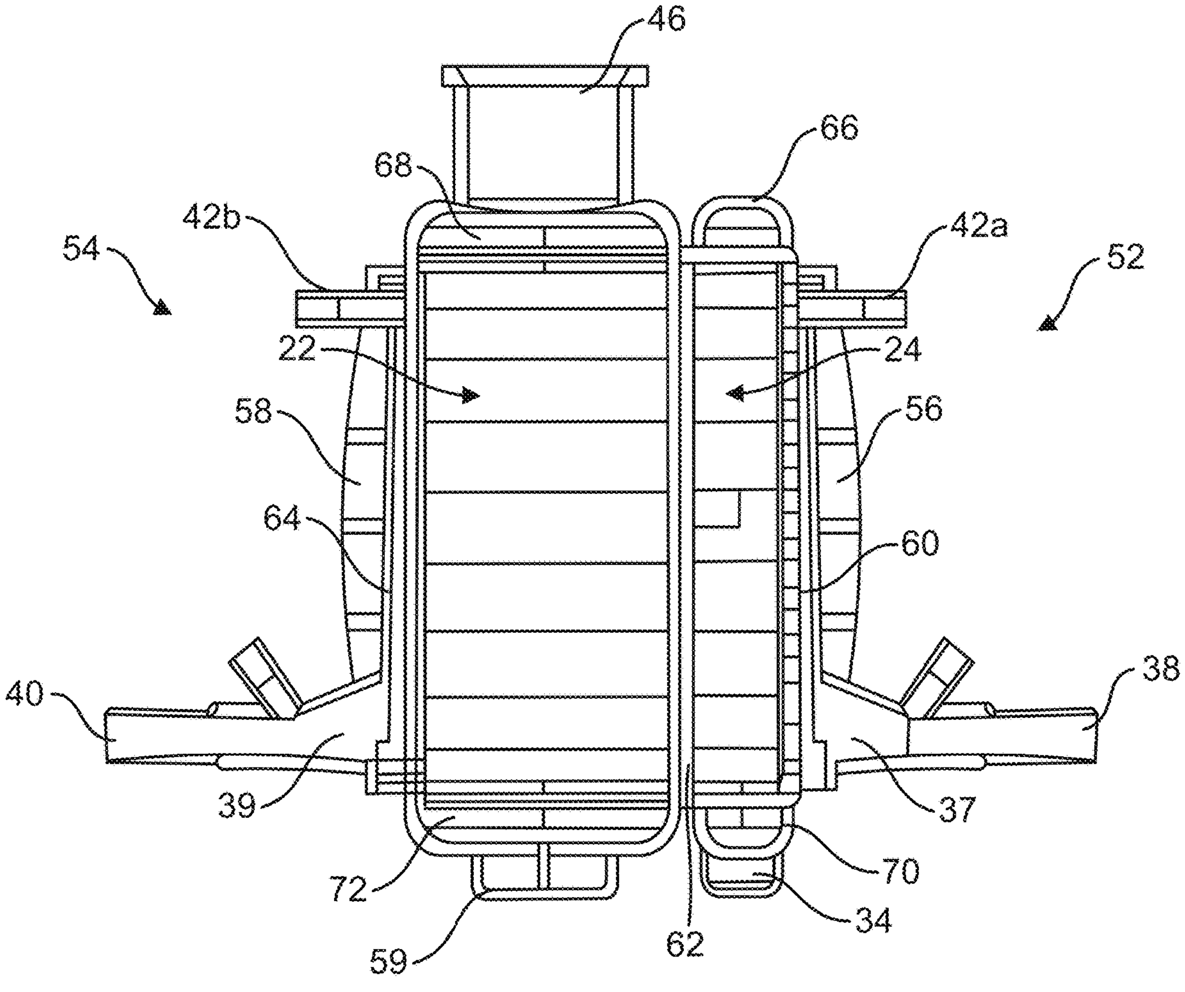
FIG. 4 is a lateral cross-section of the oxygenator device taken along line A-A of FIG. 2.

FIG. 4 illustrates a lateral cross-section of the oxygenator device 20 taken along line A-A of FIG. 2. In the illustrative embodiment of FIG. 4, the oxygenator device 20 includes the oxygenator module 22 and the heat exchanger module 24 positioned adjacent the oxygenator module 22. Both modules 22, 24 are provided with hollow fiber mat layers vertically stacked one adjacent to the other. As shown, the inlet end cap 56 includes an inlet opening 37 coupled to the inlet blood port 38 and the outlet end cap 58 includes an outlet opening 39 coupled to the outlet blood port 40.

The heat exchanger module 24 is bordered on a right side, towards the front portion 52 of the oxygenator device 20, by a blood inlet distribution grid 60. The blood inlet distribution grid 60 receives the inputted blood from the blood inlet port 38 connected to the inlet opening 37 of the inlet end cap 56 and distributes it within the blood inlet distribution grid 60 before flowing the blood into the heat exchanger module 24. Heat exchanger module 24 is bordered on the left side, towards the rear portion 54, by a separation grid 62 which provides a physical separation between the oxygenator module 22 and the heat exchanger module 24 and distributes blood flowing past the heat exchanger module 24 towards the oxygenator module 22. The heat exchanger module 24 is thus on the opposing side of separation grid 62 relative to the oxygenator module 22 which is positioned further towards the rear portion 54 of the oxygenator device 20. The heat exchanger module 24 is positioned vertically below an H/C fluid inlet chamber 66 and positioned vertically above the pedestal 59 and an H/C fluid outlet chamber 70. The oxygenator module 22 is also bordered on the left side, towards rear portion 54 of the oxygenator device 20, by a blood outlet collection grid 64 which is configured for collecting the blood flowing from the oxygenator module 22 and directing it through the outlet opening 39 of the outlet end cap 58 to the blood outlet port 40. As illustrated, vertically positioned above the oxygenator module 22 is a gas inlet chamber 68 and the bracket attachment 46. Vertically positioned below the oxygenator module 22 is the gas outlet chamber 72.

Each of the oxygenator module 22 and the heat exchanger module 24 generally include two portions, or two halves. As will be further described below, the oxygenator module 22 has a portion configured for communication with the gas inlet chamber 68 and a portion configured for communication with the gas outlet chamber 72. Similarly, the heat exchanger module 24 has a portion configured for communication with the H/C fluid inlet chamber 66 and a portion configured for communication with the H/C fluid outlet chamber 70. As illustrated, the front portion 52 of the oxygenator device 20 includes the blood inlet port 38 and the rear portion 54 of the oxygenator device 20 includes the blood outlet port 40. As a result of this configuration, when the blood is driven to pass through both the heat exchanger module 24 and the oxygenator module 22 it flows along a blood flow path from the blood inlet port 38 to the blood outlet port 40, the blood is able to come into contact (by interposition of the appropriate hollow fiber membranes in the heat exchanger module 24 and the oxygenator module 22), with the fluid and the gas mixtures for sufficient heat and gas exchange.

Figure 5:
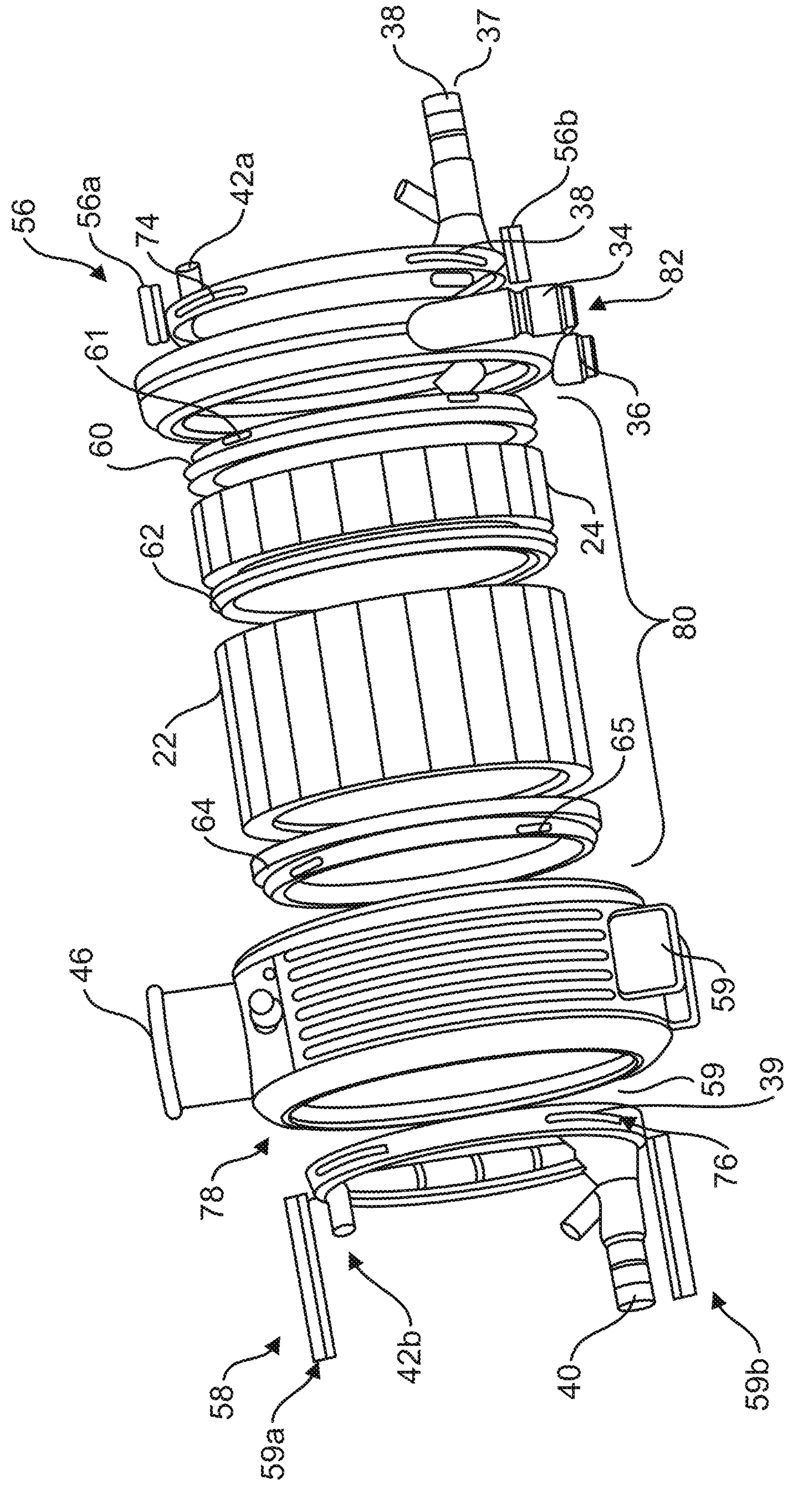
FIG. 5 is an exploded view of the oxygenator device of FIG. 2.

FIG. 5 is an exploded view of the oxygenator device 20 illustrating the component assembly within the oxygenator device 20. As shown, the oxygenator device 20 includes a blood path comprising the blood inlet end cap 56 (with the blood inlet port 38), the purging port 42*a*, the potted body 80, and the blood outlet end cap 58 (with the blood outlet port 40) and the purging port 42*b*. In various embodiments, the inlet port 38 is a separate component from the inlet end cap 56 and may be coupled or assembled with it by resin casting, such that the internal lumen of the inlet opening 37 is continuous with the internal lumen of the inlet port 38. Similarly, in various embodiment, the blood outlet port 40 is a separate component from the outlet end cap 58 and may be coupled or assembled with it by resin casting, such that the internal lumen of the outlet opening 39 is continuous with the internal lumen of the outlet port 40. The potted body 80 includes, embedded all together in one (potted) piece, the blood inlet distribution grid 60, the heat exchanger module 24, the separation grid 62, the oxygenator module 22, and the blood outlet collection grid 64. Access for H/C fluid and gas to the inner lumens of the hollow fibers of the heat exchanger 24 and oxygenator 22 is made possible through the hollow fiber open ends on the potted body outer surface.

In some embodiments, the body 80 of the oxygenator device 20 is obtained by stacking circular layers of hollow fiber mats, made, for the oxygenator 22, of polypropylene, or polymethilpentene (which are microporous materials that allow gas exchange through porosities) and, for the heat exchanger 24, of polyethylene or polyurethane (which are non-microporous materials that allow only heat exchange), potting the fiber mats with polyurethane resin and afterwards slicing the outer surface to cut open the fibers lumens so as to allow water and gas circulation inside the fiber lumens respectively of the heat exchanger and of the oxygenator. The woven fibers of each mat layer are alternatively angled vs an alignment direction by an angle $\alpha$ and an angle $\beta$ disposed on opposite sides of the alignment direction. Angles $\alpha$ and $\beta$ may be equal, or not, and are each comprised in the range 0 to 25 degrees. To provide a certain structural consistency, the layers are individually and circularly hot sealed on their external circumference. During such an operation, two orienting elements, whose function is to ease the correct stacking of the layers during the subsequent assembly of the body 80 prior to potting, are also hot sealed along the outer circumference of each layer.

In certain embodiments, the blood inlet end cap 56 is provided with a plurality of peripheral cavities 74 that mechanically fit into the corresponding peripheral notches 61 on the blood inlet distribution grid 60 of the potted body 80. Air tightness between blood inlet end cap 56 and blood inlet distribution grid 60 may be obtained by resin casting along the two circular contact surfaces of the blood inlet end cap 56 and the blood inlet distribution grid 60. Similarly, in various embodiments, on the opposite end of the potted body 80, the blood outlet end cap 58 includes a plurality of peripheral cavities 76 that mechanically fit into the corresponding peripheral notches 65 on the outlet collection grid 64 of the potted body 80. Air tightness between blood outlet end cap 58 and outlet collection grid 64 is obtained by resin casting along the circular contact surfaces of the blood outlet end cap 58 and outlet collection grid 64. In this way, the entire blood compartment, including blood inlet end cap 56, blood outlet end cap 58, potted body 80 and blood inlet/outlet ports 38 and 40 are joined in one airtight piece.

During operation, blood enters the oxygenator device 20 through the blood inlet port 38 in a direction orthogonal to the stacked hollow fiber mat layers and continues into the device through the blood inlet opening 37 of the blood inlet end cap 56, then crosses blood inlet distribution grid 60, the stacked hollow fiber mat layers forming the heat exchanger module 24, the separation grid 62, the stacked hollow fiber mat layers forming the oxygenator 22, the outlet collection grid 64, and exits the device in a direction orthogonal to the stacked hollow fiber layers by flowing through the outlet opening 39 of the blood outlet end cap 58 and through the blood outlet port 40. As shown in FIGS. 3 to 5, the blood inlet and blood outlet paths (e.g., the ports 38 and 40) to reach the inside of the oxygenator 20 are quite short. In certain embodiments, the blood inlet distribution grid 60, the separation grid 62, and the outlet collection grid 64 are circular plastic parts with relatively large bores (from 1 to 8 mm) throughout their surfaces and are configured for keeping the elements of the heat exchanger module 24 and the oxygenator module 22 in place and assuring an even distribution of blood flowing across them. The remaining parts of the device 20 comprise external housings forming an oxygenator housing enclosing the H/C fluid compartment and the gas compartment, i.e., the H/C fluid collector 82 (including the H/C fluid inlet port 34 and the H/C fluid outlet port 36) and the gas collector 78 (including the gas inlet port 30 and the gas outlet port 32, as shown in FIG. 2, and including the bracket attachment 46 and the pedestal 59).

As shown in FIG. 5, the H/C fluid collector 82 is positioned externally over the potted body 80 portion corresponding to the heat exchanger module 24 and assembled to the blood inlet end cap 56 by means of resin casting to air tighten the circular right side of the H/C fluid compartment. The left circular edge of the H/C fluid collector 82 is positioned externally in correspondence of the separation grid 62 and is air tightened to the potting body 80 by resin casting. In this way, the entire H/C fluid compartment is air tightened. The H/C fluid compartment is divided into two halves including an H/C fluid inlet chamber 66 and an H/C fluid outlet chamber 70 (shown in FIG. 4) by means of two sealing gaskets 56*a*, 56*b* which are inserted along two alignment features, illustratively two diametrically opposed and longitudinal grooves located on the outer surface of the potted body 80. The H/C fluid flows inside the H/C fluid compartment to (and from) the hollow fibers of the heat exchanger module 24 through the gap between the inner surface of the H/C fluid collector 82 and the outer surface of the potted body 80, thus forming the H/C fluid inlet chamber 66 and the H/C fluid outlet chamber 70 (shown in FIG. 4).

Similarly, as shown, the gas collector 78 is positioned externally in correspondence with the outer surface of the potted body 80 relative to the oxygenator module 22 and assembled with the blood outlet end cap 58 by means of resin casting in order to air tighten the left circular side of the gas compartment of the device 20. The right circular edge of the gas collector 78 is positioned externally next to the H/C fluid collector 82 in correspondence of the separation grid 62 and is air tightened to the potting body 80 by resin casting. In this way, the gas compartment is entirely air tightened. Also, the gas compartment is divided in two halves: a gas inlet chamber 68 and a gas outlet chamber 72 (shown in FIG. 4) by means of two sealing gaskets 59*a*, 59*b* which are inserted along two alignment features, illustratively two diametrically opposed and longitudinal grooves located on the outer surface of the potted body 80. The gas flows to (and from) the hollow fibers of the oxygenator module 22 through the gas compartment given by the gap between the inner surface of gas collector 78 and outer surface of the potted body 80, forming the gas inlet chamber 68 and the gas outlet chamber 72.

Generally, oxygenators are susceptible to gas vapor condensation. In bundled oxygenators, the gas inlet side of the hollow fibers is placed at one edge of the bundle of hollow fibers while the gas outlet is on the opposite side, in which the two sides are not adjacent to one another. The gas outlet contacts a large potting portion generally at temperatures colder than blood temperature, which is where condensation of gas vapor is likely and mainly to occur. The same phenomenon may occur with stacked oxygenators, although stacked oxygenators include hollow fibers that terminate into two gas chambers adjacently potted along the outer periphery of the layers (having polygonal or circular shape), which may expose the gas side to temperature gradients and thus cause vapor condensation. Therefore, for both oxygenator types (i.e., bundled and stacked layers), gas vapor condensation may occur more or less in a similar way.

Water droplets in the fiber lumens are undesirable. For example, water droplets in the fiber lumens may cause reductions of oxygenation capacity and $CO_2$ removal, as the water droplets create an additional barrier to gas exchange. Also, water droplets at the gas outlet port may obstruct the gas outflow path, which is always to be kept open, and generate an increase of gas side pressure. Increased gas pressure may result in conditions for embolizing the patient particularly if gas pressure exceeds blood pressure through the fiber microporosity. A capnometer (instrument measuring the $CO_2$% volume in the gas outflow) is usually connected to a line in fluid communication with the gas outlet port. When vapor is present, the capnometer may not read a correct value of $CO_2$ extraction, which is often a key parameter used to control extracorporeal circulation. This well-known phenomenon is called “wet lung” and presents a concern.

A straightforward approach to address wet lung is to flush the oxygenator manually and intermittently with a high gas flow rate for a few seconds as soon as the premonitory signs of wet lung become apparent. Such a maneuver involves a high degree of operator skill, or it may lead to blood embolization due to too high flushing flow or long flushing time. Another approach is to provide an oxygenator with a thermally insulated housing, such as an appropriate insulating material wrapped around the housing or a portion of the housing, so as to protect the oxygenator from sharp temperature drops and avoid vapor condensation. Such solution is difficult to implement and, particularly with bundled oxygenators, may hide from sight at least a large portion of the oxygenator blood compartment, which is not preferrable because clinicians typically keep the oxygenator blood compartment also under direct visual control during use.

The oxygenator 20 includes an active heating element coupled to the gas collector housing of the gas collector 78 to provide for temperature conditioning of the gas compartment that is close to the temperature of the blood to reduce vapor condensation and avoid the issues present with other attempts to address wet lung.

Figure 6:
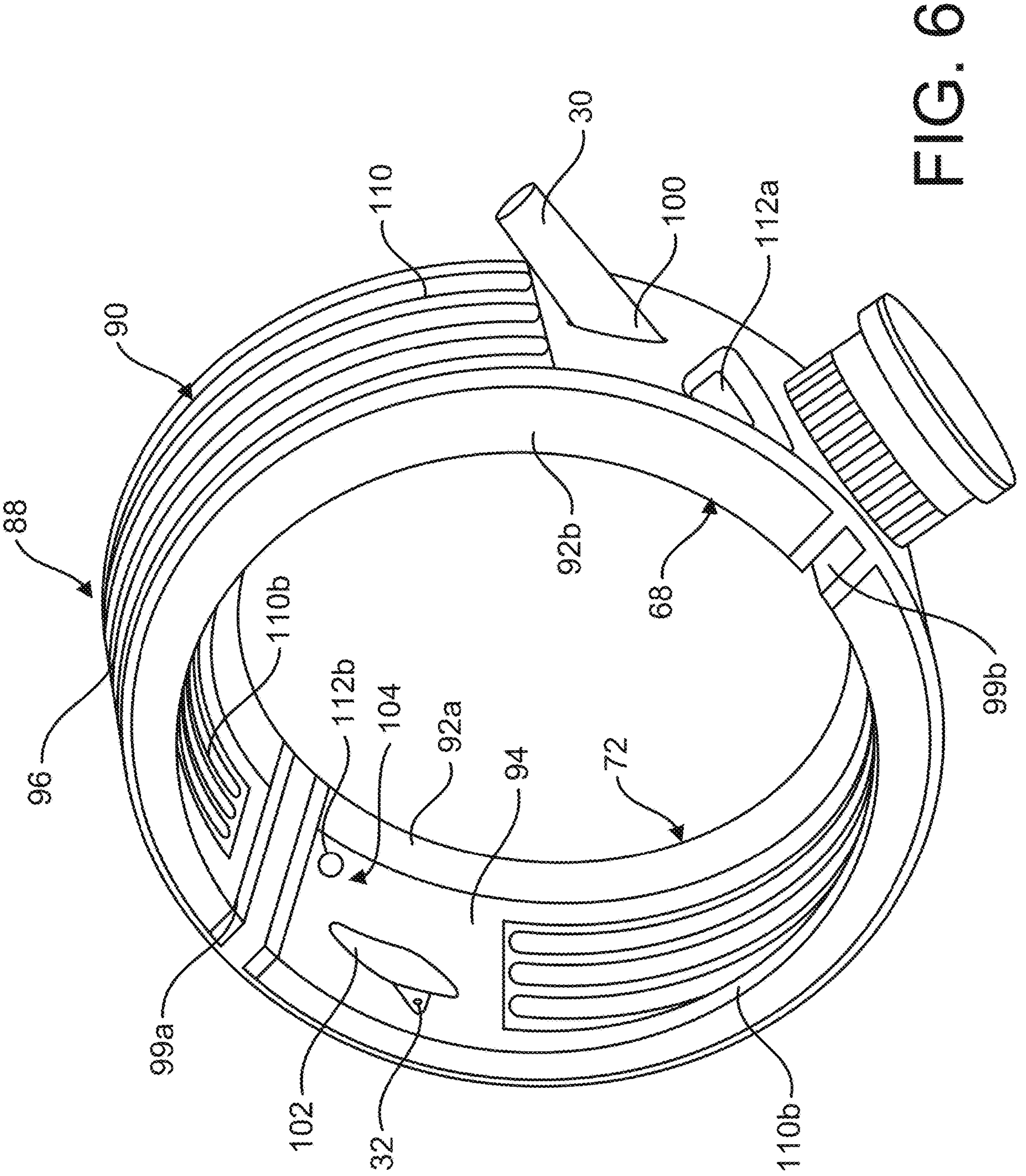
FIG. 6 is a perspective view of an example gas compartment component of the oxygenator device of FIG. 2.

FIG. 6 is a perspective side view from the right of an example gas collector housing 88 of the gas collector 78 as a section of the oxygenator housing. The exemplary gas collector housing 88 includes a ring-like cylindrical wall 90 and a pair of lateral walls 92*a*, 92*b* extending radially inward from opposing sides of the cylindrical wall 90. The lateral wall 92*a* extends from the cylindrical wall 90 to meet with the separation grid 62 at the right circular edge of the gas collector 78, and lateral wall 92*b* extends from the cylindrical wall 90 to meet with the outlet collection grid 64 at the left circular edge of the gas collector 78 in FIG. 5. Further, the cylindrical wall 90 includes a major inner surface 94, disposed between the lateral walls 92*a*, 92*b*, and an opposing major outer surface 96. In the illustrated embodiment, the major inner surface 94 includes diametrically opposed guides 99*a*, 99*b* configured to receive sealing gaskets 59*a*, 59*b*, respectively, of FIG. 5. The major inner surface 94 is spaced-apart from the hollow fibers, such as the hollow fiber open ends on the potted body outer surface. The gas collector housing 88 defines the inlet port 30 and outlet port 32. In the illustrated embodiment, the cylindrical wall 90 includes an inlet opening 100 in communication with the inlet port 30 and an outlet opening 102 in communication with outlet port 32 of FIG. 2. The gas collector housing 88 interior defines a gas compartment 104 in fluid communication with the gas inlet port 30 and the gas outlet port 32. The gas compartment 104 in embodiments is further defined into the gas inlet chamber 68 in fluid communication with the gas inlet port 30 and the gas outlet chamber 72 in fluid communication with the gas outlet port 32. For instance, when coupled with sealing gaskets 59*a*, 59*b* and the oxygenator of the potted body 80, the gas collector 78 forms gas inlet chamber 68 and gas outlet chamber 72.

A heating device 110 is disposed against the gas collector housing 88 proximate the gas compartment 104 such as disposed within one or more of the chambers 68, 72 and spaced-apart from the hollow fibers such as the hollow fiber open ends of the potted body outer surface. In one example, the heating device 110 is disposed against the major inner surface 94 of the cylindrical wall 90 such as a first, or inlet chamber heating device 110*a* disposed between the inlet opening 100 and the generally opposing guide 99*a* and a second, or outlet chamber heating device 110*b* disposed between the outlet opening 102 and the generally opposing guide 99*b*. In the illustrated embodiment, the heating device 110 is a flexible heating device. In another embodiment, the flexible heating device includes a first heating device disposed along the major inner surface of the inlet chamber 110*a* between guides 99*a*, 99*b* with an opening formed on the flexible heating device for the inlet opening 100, and a second heating disposed along the major inner surface 94 of the outlet chamber 110*b* between guides 99*a*, 99*b* with an opening formed on the flexible heating device for the outlet opening 102.

In some embodiments, a temperature sensor 112 is included in the gas compartment 104 with the heating device 110. For example, the gas inlet chamber 68 includes a first, or gas inlet temperature sensor 112*a* associated with the first heating device 110*a*, and the gas outlet chamber 72 includes a second, or gas outlet temperature sensor 112*b* associated with the second heating device 110*b*. In some embodiments, only one temperature sensor, such as temperature sensor 112*b*, is provided and associated with heating element 110*b*. In embodiments, the heating device 110 and temperature sensor 112 are coupled to a controller (not shown).

During operation of the oxygenation device 20, the heating device 110 is configured to heat the gas compartment. In particular, the inlet chamber heating device 110*a* is configured to heat the gas inlet chamber 68, and the outlet chamber heating device 110*b* is configured to heat the gas outlet chamber 72. The simultaneous application of multiple heating devices 110, such as the heating device 110*a* in the gas inlet chamber 68 and the heating device 110*b* in the gas outlet chamber 72, makes it possible to heat gas compartment at a temperature close to that of the blood, which provides for efficient protection against wet lung versus an application of a single heating device, such as a heating device only in the gas outlet chamber 72. The heating device 110 in some embodiments is electrically connected to the controller 21 to receive a power signal such as from a direct current (DC) power supply. The power signal causes a heating element in the heating device to become warm. The application of the heating device 110 to heat the gas compartment 104 is based on a temperature determined by the temperature sensor 112. For example, the first heating device 110*a* can be independently applied to heat the gas inlet chamber 68 from the second heating device 110*b*, which second heating device 110*b* can be independent applied to heat the gas outlet chamber 72 from the first heating device 110*a*. In another embodiment, the controller can base the operation of the first and second heating devices 110*a*, 110*b* on one or both of the temperature sensors 112*a*, 112*b*. In some embodiments, the temperature sensor 112 is a separate component within the gas compartment 104, and in some embodiments, the temperature sensor 112 is integrated into the heating device 110. In some embodiments, the temperature sensor is disposed outside of the gas compartment, such as on the major outer surface 96. In some examples, the temperature sensor 112 is electrically coupled to the controller 21 to provide the controller 21 with an electrical temperature signal on which to base the power signal provided to the heating device 110 in a feedback system. For instance, the controller 21 can compare the temperature of the gas compartment based on the temperature sensor 112 to the temperature of the blood based on other sensors. The control 21 can adjust the power signal to the heating device 110 based on the difference between the temperature of the gas compartment and the temperature of the blood. In one example, the controller 21 attempts to maintain the temperature of the gas compartment within each of the gas inlet chamber and the gas outlet chamber to be at the temperature of the blood. In another embodiment, the controller 21 can receive a selected temperature value from an operator, and the controller 21 attempts to maintain the temperature of the gas compartment within each of the gas inlet chamber and the gas outlet chamber to be at the selected temperature. In still another embodiment, the controller can attempt to maintain the temperature in each chamber at separate selected temperatures.

Figure 7:
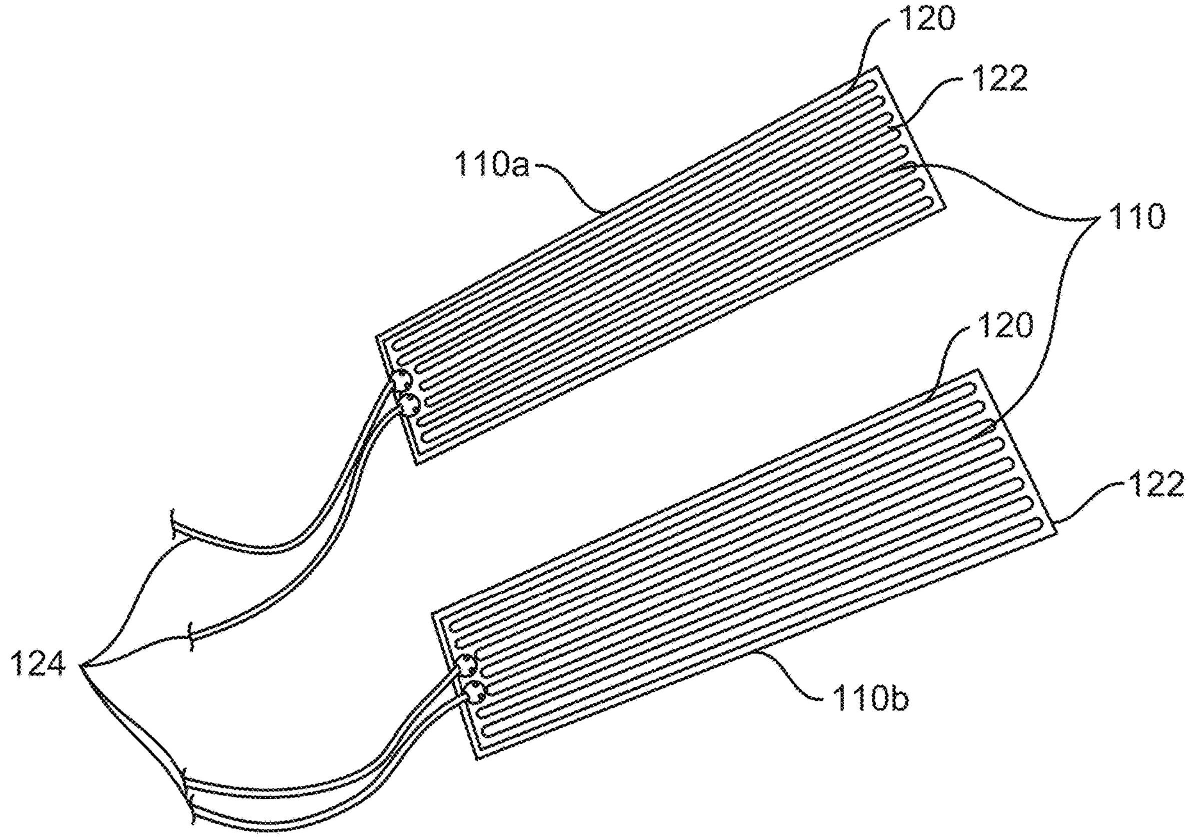
FIG. 7 is a perspective view of an example heating device for use with the oxygenator device of FIG. 2.

FIG. 7 illustrates an embodiment of heating device 110 configured as a flexible thermofoil. The flexible thermofoil embodiment of the heating device 110 includes a thin, flexible component having a foil resistive heating element 120 laminated between layers of flexible and electrically insulative substrate 122. An electrical signal is provided to the heating element 120 via an electrical connection 124, such as lead wires welded to the heating element 120. Other electrical connections can include electrical connectors, flex circuits or solder pads. The heating device 110 can include one heating element or more than one heating elements to precisely direct heat or act as a redundancy. The heating element 120 can be constructed from an electrically conductive but not magnetic alloy for inductance canceling. In some embodiments, multiple layers of heating elements are included in the thermofoil. In one embodiment, the substrate 122 is constructed from polyimide. The heating device 110 can be coupled to the major inner surface 94 of the gas collector housing 88 via an adhesive, such as a pressure sensitive adhesive. The electrical connections 124 extend out of the housing 88, such as through holes (not shown) that are then sealed air-tight to prevent gas from leaking from the gas compartment 104. In some embodiments, a temperature sensor, such as temperature sensor 112, can be attached to or formed on the substrate 122 and electrically coupled to a separate electrical connection. The thin construction provides for effective temperature conditioning of the gas compartment 104 and, in turn, of the passing gas through the gas compartment without unduly affecting gas pressure with the gas compartment 104. In some examples, the heating device is available as a thermofoil from MINCO of Minneapolis, Minnesota.

Figure 8:
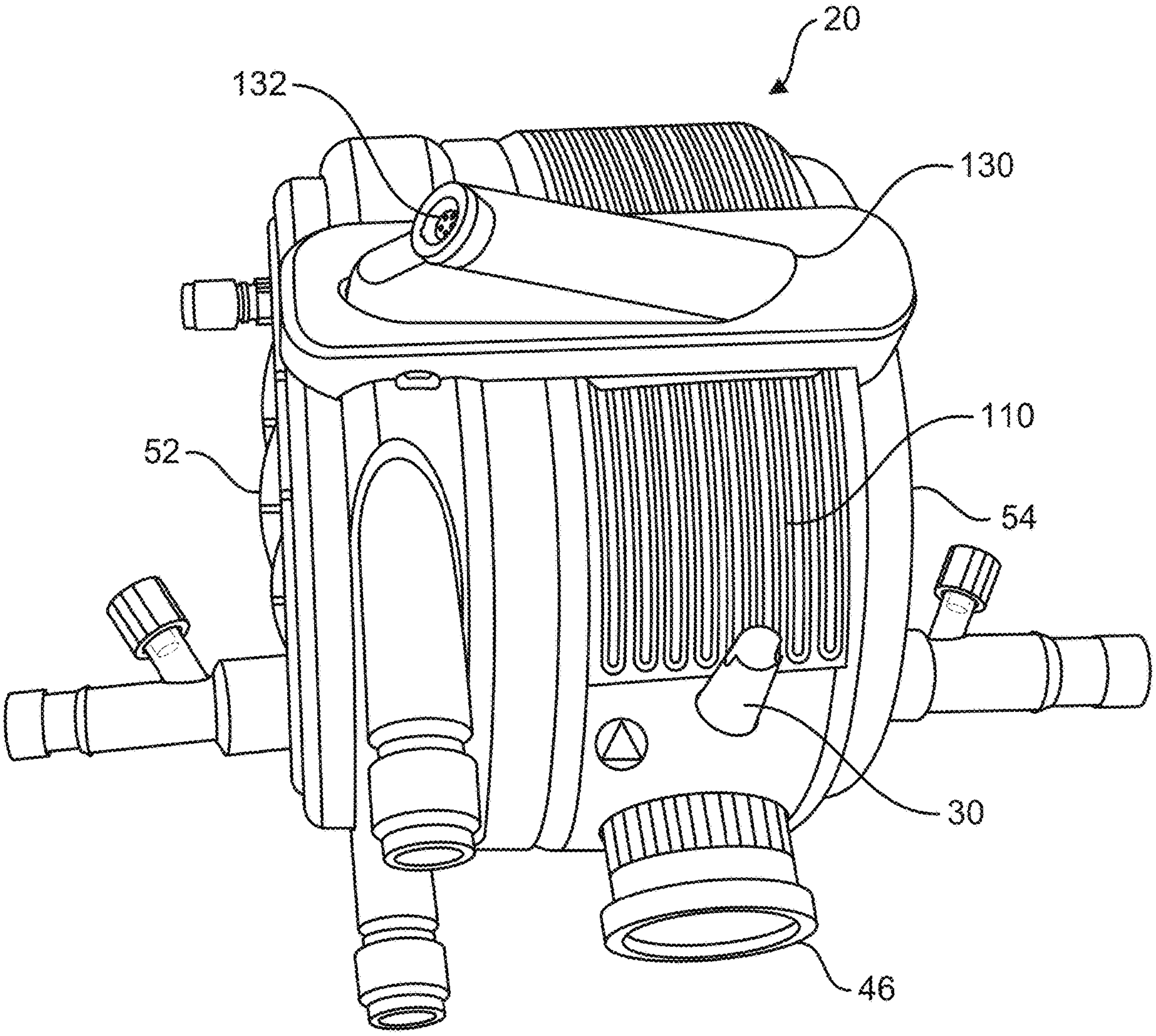
FIG. 8 is a perspective view of the example of the oxygenator device of FIG. 2.

FIG. 8 illustrates the oxygenator device 20 from a different perspective. The oxygenator device 20 includes a manifold 130 coupled to the oxygenator housing such as the gas collector housing 88. The electrical leads for the heating devices 110 and temperature sensors 112 are collected within the manifold 130 and presented in an electrical connector 132. The electrical connector 132 can be electrically and mechanically coupled to an electrical cable that is electrically coupled to the controller 21.

In one example, oxygenator devices with a gas compartment heating device were invitro gas transfer tested for 6 hours with bovine blood, at 7 liters per minute (lpm) blood flow rate and 1:1 gas to blood flow ratio. The gas compartment heating device was realized by using two rectangular flexible thermofoils, one inside the gas inlet chamber and the other inside the gas outlet chamber, and each of them having the following characteristics: polyester substrate with a pressure sensitive adhesive on the back side to bond the substrate to the major inner surface; total electrical resistances: approx. 25 ohms, supply voltage was DC 12 V or DC 24 V; rectangular shape: 150 mm length, 40 mm width; power consumption: 0.3-0.5 W/$cm^2$. During the test the temperature of the gas collector surface was kept at approximately 36.5° C. as measured in open loop by a single temperature sensor placed in contact with the major outer surface of the gas collector with a controller supplying the gas heating device at 5 V and 0.38 Amp. Blood temperature was maintained at approximately 36.5-37° C. By changing the supply voltage level, the collector temperature was also changed.

This configuration was sufficient to avoid vapor condensation inside the oxygenator device throughout the test. The gas pressure delta (in-out) remained constant for the 6-hour test. Also, all the gas exchange parameters, either in terms of oxygenation ($O_2$TR in cc/min) or $CO_2$ removal ($CO_2$TR in cc/min), remained constant or had negligeable variations. There was never the need of flushing the fiber gas inner lumens with a gas flow. Also, a capnometer connector derived from the gas outlet port of the oxygenator was clean and free from condensation throughout the test duration.

In contrast, in the same type of in vitro test with several comparison oxygenators lacking the heating device, also conducted at 7 lpm and 1:1 gas to blood flow ratio, vapor condensation occurred and accumulated at the gas outlet port starting from the third hour of the test. Gas pressure delta increases throughout the test (sometimes, from approximately 40 mm$H_2O$ initial value to approximately 100 mm$H_2O$ final value). Also, oxygenation and CO2 removal did decreased in tests, more pronounceably during the second half of the 6 hour test, and flushing with gas of the fiber inner lumens at times was necessary, including several times during the test, to maintain acceptable performance. Despite gas flushing, restoration of performance was more partial than complete and always temporary.

Figure 9A:
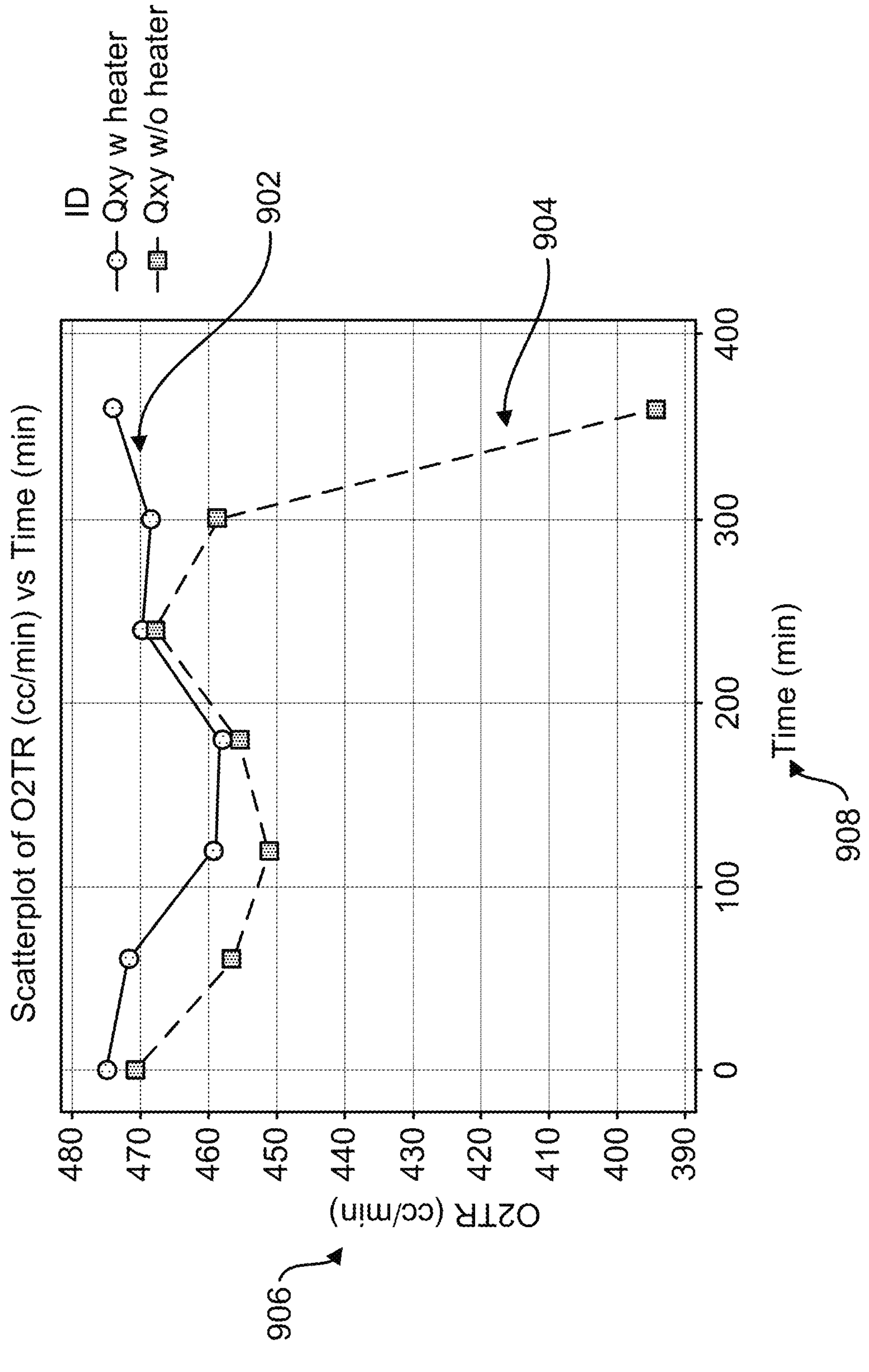
FIGS. 9A-9C are graphs illustrating performance over a period time of oxygenator devices of the present disclosure versus typical oxygenator devices.
Figure 9B:
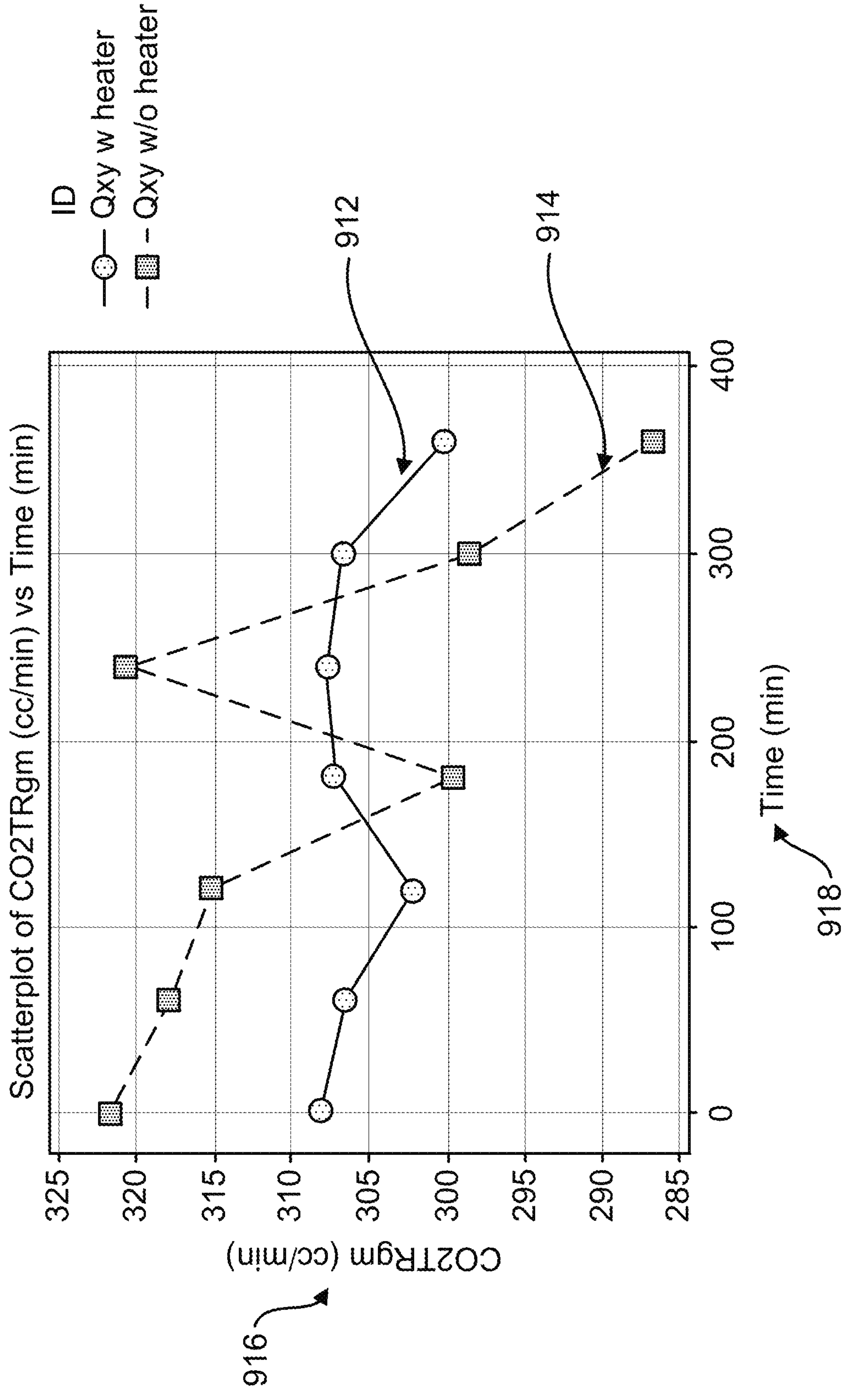
Figure 9C:
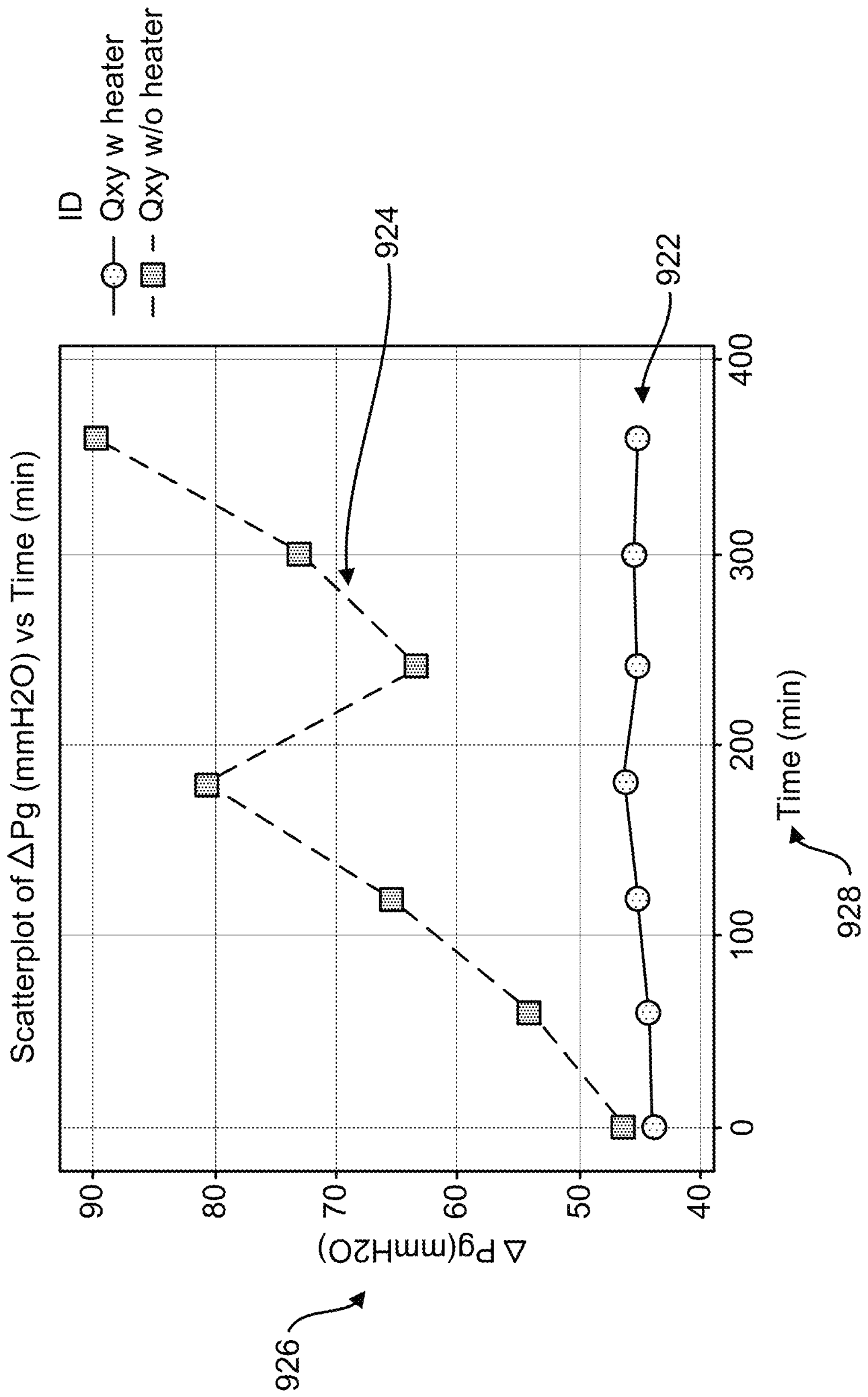

FIGS. 9A-9C illustrate various graphs of performance of the example, the average of two oxygenator devices with a gas compartment heating device against an average of four comparison oxygenator devices without gas compartment heating devices over the same periods of time in the procedures. FIG. 9A illustrates the performance of the example oxygenator devices, along plot line 902, and the average of comparison oxygenator devices during the tests, along plot line 904, for oxygenation ($O_2$TR in cc/min) 906 over a period of time in minutes 908. FIG. 9B illustrates the performance of the example oxygenator device, along plot line 912, and the average of comparison oxygenator devices during the tests, along plot line 914, for $CO_2$ removal ($CO_2$TR in cc/min) 916 over a period of time in minutes 918. FIG. 9C illustrates the performance of the example oxygenator device, along plot line 922, and the average of comparison oxygenator devices during the tests, along plot line 024, for gas pressure delta 926 over a period of time in minutes 928. Some of the comparison oxygenators had their gas sides flushed with air between the third and fourth hour (180-240 minutes of the test, which allowed a partial and temporary recovery of $O_2$TR, $CO_2$TR (going up towards the optimal values measured at time 0 when water condensation was not present) and gas pressure delta (going down towards the optimal values measured at time 0, when water condensation was not present).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An oxygenation device for use in connection with extracorporeal blood circulation, the device comprising:

an oxygenator housing including a blood inlet end cap defining a blood inlet opening, a blood outlet end cap defining a blood outlet opening and a blood flow path between the blood inlet opening and the blood outlet opening, and a gas collector housing disposed between the blood inlet opening and the blood outlet opening, the gas collector housing defining a gas inlet port, a gas outlet port and a gas compartment having a gas inlet chamber in fluid communication with the gas inlet port and a gas outlet chamber in fluid communication with the gas outlet port;

a plurality of hollow fibers disposed inside the oxygenator housing and along the blood flow path, the hollow fibers fluidly coupled to the gas compartment; and a plurality of heating devices disposed against the gas collector housing, the plurality of heating devices including a first heating device disposed in the gas inlet chamber and a second heating device disposed in the gas outlet chamber, wherein during operation of the oxygenation device, the plurality of heating devices are configured to heat the gas compartment.

2. The device of claim 1, wherein the plurality of hollow fibers disposed inside the housing include a plurality of stacked, mat layers of the hollow fibers.

3. The device of claim 1, wherein the oxygenator housing further comprises a heat exchanger housing for a heat exchanger module adjacent to the oxygenator housing.

4. The device of claim 3, wherein the heat exchanger housing defines a fluid inlet port and a fluid outlet port and is configured such that a H/C fluid may pass through the plurality of hollow fibers.

5. The device of claim 1, wherein the oxygenator housing is configured such that a gas mixture may enter through the gas inlet port, pass through the plurality of hollow fibers and exit through the gas outlet port.

6. The device of claim 1, and further comprising a temperature sensor disposed in the gas collector housing.

7. The device of claim 6, wherein the temperature sensor includes a first temperature sensor disposed in the gas inlet chamber and a second temperature sensor disposed in the gas outlet chamber.

8. The device of claim 7, and further comprising a remote monitoring unit communicatively coupled to each of the first and second temperature sensors.

9. The device of claim 8, wherein the remote monitoring unit is configured to operate the heating devices to heat the gas in the gas compartment to the temperature of blood in the device.

10. The device of claim 6, and further comprising a manifold coupled to the oxygenator housing to receive electrical leads from the heating device and the temperature sensor.

11. The device of claim 10, wherein the manifold includes an electrical connection.

12. The device of claim 1, wherein each of the plurality of heating device includes a flexible heating device having an electrical element disposed on a flexible electrically-insulative substrate.

13. The device of claim 12, wherein the gas compartment includes a generally cylindrical major inner surface defined in the gas inlet chamber and the gas outlet chamber, and the plurality of flexible heating devices are adhered to the major inner surface.

14. The device of claim 13, wherein the plurality of flexible heating devices are spaced-apart from the plurality of hollow fibers.

15. An oxygenation system for use in connection with extracorporeal blood circulation, the system comprising:

an oxygenator housing including a blood inlet end cap defining a blood inlet opening, a blood outlet end cap defining a blood outlet opening and a blood flow path between the blood inlet opening and the blood outlet opening, and a gas collector housing disposed between the blood inlet opening and the blood outlet opening, the gas collector housing defining a gas inlet port, a gas outlet port and a gas compartment having a gas inlet chamber in fluid communication with the gas inlet port and a gas outlet chamber in fluid communication with the gas outlet port;

a plurality of hollow fibers disposed inside the oxygenator housing and along the blood flow path, the hollow fibers fluidly coupled to the gas compartment;

a plurality of heating devices disposed against the gas collector housing, the plurality of flexible heating elements including a first heating device disposed in the gas inlet chamber and a second heating device disposed in the gas outlet chamber; and a remote monitoring unit communicatively coupled to the plurality of heating devices, wherein during operation of the system the remote monitoring unit is configured to provide a heating signal to the plurality of heating devices to heat gas in the gas compartment.

16. The system of claim 15, and further comprising a temperature sensor disposed on the gas collector housing and communicatively coupled to the remote monitoring unit, wherein during operation of the system the remote monitoring is configured to receive a temperature signal from the temperature sensor on which to base the heating signal.

17. The system of claim 16, wherein the temperature sensor includes a first temperature sensor disposed in the gas inlet chamber and a second temperature sensor disposed in the gas outlet chamber, the first temperature sensor configured to provide a first temperature signal to the remote monitoring unit, and the second temperature sensor configured to provide a second temperature signal to the remote monitoring unit.

18. The system of claim 17, wherein the heating signal includes a first heating signal provided to the first heating device and a second heating signal provided to the second heating device.

19. The system of claim 18, wherein the remote monitoring unit provides the first heating signal is based on the first temperature signal and the second heating signal based on the second temperature signal.

20. The system of claim 15, wherein the plurality of hollow fibers disposed inside the housing include a plurality of stacked, mat layers of the hollow fibers.

* * * * *